(12) United States Patent
Al-Jenoobi et al.

(10) Patent No.: US 11,617,726 B2
(45) Date of Patent: Apr. 4, 2023

(54) METHOD FOR PREVENTING, TREATING, OR AMELIORATING A MICROBIAL INFECTION

(71) Applicant: KING SAUD UNIVERSITY, Riyadh (SA)

(72) Inventors: Fahad Ibrahim Al-Jenoobi, Riyadh (SA); Mohd Aftab Alam, Riyadh (SA); Mohamed Hamed Al-Agamy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/723,773

(22) Filed: Dec. 20, 2019

(65) Prior Publication Data

US 2020/0138745 A1    May 7, 2020

Related U.S. Application Data

(62) Division of application No. 16/182,906, filed on Nov. 7, 2018, now Pat. No. 10,568,849.

(51) Int. Cl.
| | |
|---|---|
| *A61K 36/00* | (2006.01) |
| *A61K 31/122* | (2006.01) |
| *A61P 31/04* | (2006.01) |
| *A61K 47/44* | (2017.01) |
| *A61K 9/107* | (2006.01) |

(52) U.S. Cl.
CPC .......... *A61K 31/122* (2013.01); *A61K 9/1075* (2013.01); *A61K 47/44* (2013.01); *A61P 31/04* (2018.01)

(58) Field of Classification Search
None
See application file for complete search history.

(56) References Cited

U.S. PATENT DOCUMENTS

| | | |
|---|---|---|
| 2009/0246292 A1 | 10/2009 | Seville et al. |
| 2011/0076346 A1 | 3/2011 | Babish |
| 2016/0101124 A1 | 4/2016 | Halwani et al. |

FOREIGN PATENT DOCUMENTS

JP    2017193489 A    10/2017

OTHER PUBLICATIONS

Mohamed Eisa Adam, "Antimicrobial Activity of Bee Honey, Black Cumin Oil and Green Tea Against Multi-Drug Resistant Pathogenic Bacteria," Int'l J. of Curr. Micro. and App. Sci., 2(12): pp. 58-63 (2013).
Al-Jaafary Maryam et al., "In-vitro studies on the effect of *Nigella sativa* Linn., seed oil extract on Multidrug resistant Gram positive and Gram negative bacteria," J. of Med. Plants Studie, 4(2): pp. 195-199 (2016).
Salman et al., "Antimicrobial activity of *Nigella sativa* Linn. seed oil against multi-drg resistant bacteria from clinical isolates", Natural Product Radiance (2008), vol. 7(1), pp. 10-14.
Saleh et al., "Phytochemical Analysis of *Nigella sativa* L. Utilizing GC-MS Exploring its Antimicrobial Effects against Multidrug-Resistant Bacteria", Pharmacog J. (2018), vol. 10(1), pp. 99-105.

*Primary Examiner* — Qiuwen Mi
(74) *Attorney, Agent, or Firm* — Nath, Goldberg & Meyer; Richard C. Litman

(57) ABSTRACT

A method for preventing, treating, or ameliorating a microbial infection can include administering thymoquinone or a pharmaceutical composition comprising thymoquinone to a patient in need thereof. The patient may be suffering from a microbial infection caused by gram-negative bacteria, gram-positive bacteria, or fungi. The microbial infection may be caused by gram negative bacteria. The gram-negative bacteria may include *Acinetobacter baumannii*. The gram-negative bacteria may include *Pseudomonas aeruginosa*. The microbial infection may be caused by antimicrobial sensitive *Acinetobacter baumannii* or antimicrobial resistant *Acinetobacter baumannii*.

4 Claims, No Drawings

METHOD FOR PREVENTING, TREATING, OR AMELIORATING A MICROBIAL INFECTION

CROSS REFERENCE TO RELATED APPLICATION

This application is a divisional of application Ser. No. 16/182,906, filed Nov. 7, 2018, now issued.

BACKGROUND

1. Field

The disclosure of the present patent application relates to antimicrobial agents, and particularly to a thymoquinone antimicrobial agent and its use against drug-susceptible and drug-resistant microbial infections.

2. Description of the Related Art

Pathogenic microorganisms such as bacteria and fungi cause infections in humans and animals. Sometimes it is difficult to treat these infections using available antimicrobial agents. In particular, the treatment of life-threatening infections caused by resistant pathogenic microorganisms is a challenging task. In drug resistant cases, pathogenic microorganisms have reduced or lost their susceptibility to one or more antimicrobial agents. Antimicrobial resistance reduces the efficacy of antimicrobial drugs or renders the drug(s) ineffective against targeted microbe(s) at a standard dose. Treatment of infections caused by resistant microbes is difficult, complicated and expensive. In such cases, patients' suffering is prolonged and chances of mortality are increased. Multidrug resistance limits the therapeutic options available for treatment of infections and forces healthcare providers to use comparatively higher doses or more toxic and/or expensive antimicrobial agents.

Gram-negative infections are typically due to common pathogens such as *Acinetobacter, Pseudomonas aeruginosa,* and the Enterobacteriaceae family. *Acinetobacter baumannii* infections are typically hospital-derived infections.

Thus, a method for treating microbial infections solving the aforementioned problems is desired.

SUMMARY

A method for preventing, treating, or ameliorating a microbial infection can include administering thymoquinone or a pharmaceutical composition comprising thymoquinone to a patient in need thereof. The microbial infection may be caused by gram-negative bacteria, gram-positive bacteria, or fungi. The gram-negative bacteria may include *Acinetobacter baumannii*. The gram-negative bacteria may include *Pseudomonas aeruginosa*. The microbial infection may be caused by antimicrobial sensitive *Acinetobacter baumannii* or antimicrobial resistant *Acinetobacter baumannii*. The pharmaceutical composition may be formulated as a microemulsion.

These and other features of the present disclosure will become readily apparent upon further review of the following specification and drawings.

DETAILED DESCRIPTION OF THE PREFERRED EMBODIMENTS

A method for preventing, treating, or ameliorating a microbial infection can include administering thymoquinone or a pharmaceutical composition comprising thymoquinone to a patient in need thereof. The patient may include a human or an animal. The microbial infection may be caused by gram-negative bacteria, gram-positive bacteria, or fungi. The microbial infection may be caused by gram negative bacteria. The gram-negative bacteria may include *Acinetobacter baumannii*. The gram-negative bacteria may include *Pseudomonas aeruginosa*. The microbial infection may be caused by antimicrobial sensitive *Acinetobacter baumannii* or antimicrobial resistant *Acinetobacter baumannii*.

As used herein, the term "about" when modifying a numerical value shall mean within 10% of the modified numerical value.

Thymoquinone (2-isopropyl-5-methylbenzo-1, 4-quinone) is a bioactive molecule. Thymoquinone has been reported to have anti-oxidant activity, anti-inflammatory activity, and anti-cancer activity. Thymoquinone has also demonstrated protective effects on several organs against oxidative damage.

A pharmaceutical composition comprising thymoquinone can include thymoquinone and at least one pharmaceutically acceptable excipients. Pharmaceutically acceptable excipients can be selected from carriers, diluents, stabilizers, complexing agents, buffers, binders, emulsifiers, surfactants, solubilizers, thickeners, suspending agents, hydrophobic ointment base, gel forming polymers, lubricants, colors, flavors, and preservatives. In an embodiment, the pharmaceutical composition comprising thymoquinone is formulated as a microemulsion including thymoquinone, an oil, a surfactant, and water. In an embodiment, the pharmaceutical composition includes from about 0.01% to about 1.0% w/v thymoquinone, from about 2% to about 6% by volume oil, from about 25% to about 40% by volume surfactant, and a remainder of the pharmaceutical composition includes water.

The pharmaceutical composition may include at least one supplementary antimicrobial agent. The thymoquinone and the at least one supplemental antimicrobial agent can be in intimate contact in the pharmaceutical composition. The thymoquinone and the at least one supplemental antimicrobial agent in the pharmaceutical composition may be separated by a barrier. The thymoquinone and the at least one additional supplemental antimicrobial agent can be separately formulated, but simultaneously used.

The supplemental antimicrobial agent can include at least one of the following: aminoglycosides (Amikacin, Gentamicin, Kanamycin, Neomycin, Netilmicin, Tobramycin, Paromomycin, Streptomycin), Ansamycins (Geldanamycin, Rifaximin), Carbapenems (Ertapenem, Doripenem, Imipenem/Cilastatin, Meropenem), Cephalosporins (Cefadroxil, Cefazolin, Cefalexin, Cefaclor, Cefprozil, Cefuroxime, Cefixime, Cefdinir, Cefditoren, Cefoperazone, Cefotaxime, Cefpodoxime, Ceftazidime, Ceftibuten, Ceftriaxone, Cefepime, Ceftaroline fosamil, Ceftobiprole) Glycopeptides (Teicoplanin, Vancomycin, Telavancin, Dalbavancin, Oritavancin) Lincosamides (Clindamycin, Lincomycin) Lipopeptide (Daptomycin) Macrolides (Azithromycin, Clarithromycin, Erythromycin, Roxithromycin, Telithromycin, Spiramycin) Monobactams (Aztreonam) Nitrofurans (Furazolidone, Nitrofurantoin) Oxazolidinones (Linezolid, Posizolid, Radezolid, Torezolid) Penicillins (Amoxicillin, Ampicillin, Azlocillin, Dicloxacillin, Flucloxacillin, Mezlocillin, Methicillin, Nafcillin, Oxacillin, Piperacillin) Penicillin combinations (Amoxicillin/clavulanate, Ampicillin/sulbactam, Piperacillin/tazobactam, Ticarcillin/clavulanate) Polypeptides (Bacitracin, Colistin, Polymyxin B) Quinolones/Fluoroquinolones (Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, Temafloxacin) Sulfonamides (Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Co-trimoxazole, Sulfonamidochrysoidine) Tetracyclines (Demeclocycline, Doxycycline, Metacycline, Minocycline, Oxytetracycline, Tetracycline) Anti-mycobacterials (Capreomycin, Cycloserine, Ethambutol, Ethionamide, Isoniazid, Pyrazinamide, Rifampicin, Rifabutin, Rifapentine, Streptomycin) other antibiotics (Arsphenamine, Chloramphenicol, Fosfomycin, Fusidic acid, Metronidazole, Mupirocin, Thiamphenicol, Tigecycline), essential oils and their active constituents (Clove oil, Eugenol, Cinnamaldehyde), and myrrh (*Commiphora myrrha*) and its active ingredients.

The methods described herein may be used to prevent, treat, or ameliorate microbial infections caused by gram-positive bacteria, gram negative bacteria, or fungi. The methods may be used to prevent, treat, or ameliorate antimicrobial sensitive as well as antimicrobial resistant microorganisms.

The pathogenic gram-positive bacteria may include *Staphylococcus* (e.g., *S. epidermis* and *S. aureus*); *Corynebacterium* (e.g., *C. pyogenes* and *C. pseudotuberculosis*); *Micrococcus*; *Streptococcus* (e.g., *S. pyogenes, S. equis, S. zooepidemicus, S. equisimilis, S. pneumoniae* and *S. agalactiae*); *Erysipelothrix* (e.g, *E. rhusiopathiae*); *Bacillus* (e.g., *B. anthracis*); *Listeria* (e.g., *L. monocytogenes*); *Clostridium* (*C. perfringens*); and *Mycobacterium* (*M. tuberculosis* and *M. leprae*). Animal or human subjects infected with these pathogens may be detected by established methods.

The pathogenic gram negative bacteria infection may include Enterobacteriaceae (*Escherichia*, e.g., *E. coli; Citrobacter; Enterobacter; Shigella; Salmonella; Edwardsiella; Hafnia; Klebsiella*, e.g., *K. pneumoniae; Morganella; Proteus; Providencia; Serratia; Yersinia*); Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella*, Spirochaetaceae (*Treponema* and *Borrelia*), Bacteroidaceae (*Bacteroides, Fusobacterium, Prevotella, Porphyromonas*), Leptospiraceae, *Campylobacter, Helicobacter, Spirillum, Streptobacillus, Acinetobacter*, especially *Acinetobacter baumanii*. Animal or human subjects infected with these pathogens may be detected by established methods.

The pathogenic fungi may include *Candida* (e.g., *C. albicans*); *Malassezia* (e.g., M dermatis); *Coccidioides* (e.g., *C. immitis*); *Penicillium* (e.g., *P. marneffei*); and *Pneumocystis* (e.g., *P. carinii*); *Hyphomyces* (e.g., *H. destruens*); *Cryptococcus* (e.g., *C. neoformans*); *Aspergillus* (e.g., *A. fumigatus*); *Histoplasma* (e.g., *H. capsulatum*); *Blastomyces* (e.g., *B. dermatiditis*); *Rhinosporidium; Sporothrix*; and dermatophytes. Animal or human subjects infected with these pathogens may be detected by established methods.

In an embodiment the pharmaceutical composition may be administered to a human or animal patient in a suitable form. A suitable form for topical administration (skin and mucous membrane) may include a topical ointment, cream, micro-emulsion, nano-emulsion, spray, lotion, oil, powder, liniment, solution, or a gel. A suitable form for oral administration may include a tablet, capsule, pellet, granules, solution, lozenge, suspensions, emulsions, micro-emulsion, or a nano-emulsion. The pharmaceutical composition can also be formulated as injectable solution, powder ready for reconstitution for injection, inhalant, or a suppository.

In an embodiment, the pharmaceutical composition may be formulated as a microemulsion. The microemulsion can include thymoquinone, an oil, at least one of a surfactant and a co-surfactant, and water. The oil can be selected from fixed oils and essential oils.

In an embodiment the thymoquinone antimicrobial agent may be protected from light and packaged in suitable light resistant container. The thymoquinone antimicrobial agent may be packaged in aluminum tubes, light resistant plastic tubes, light resistant bottles or jar like containers, or in light resistant blister packaging.

In an embodiment, the pharmaceutical composition may be delivered topically to the patient via a dressing comprising thymoquinone. The dressing may also comprise an additional antimicrobial agent along with thymoquinone. Suitable dressings may include bandages, gauzes, tissues, films, gels, or foams.

In an embodiment, the pharmaceutical composition may be provided for systemic use. For systemic use, the pharmaceutical composition can be administered orally, parenterally (intravenous, intramuscular, or subcutaneous injections), or by the nasal route (through solution or inhalator or spray).

In an embodiment, the pharmaceutical composition may be provided for topical use. For topical use, the pharmaceutical composition may be administered on the skin or on a mucous membrane (e.g., buccal mucosa, eyes and ears, rectal mucosa, vaginal mucosa) of the patient.

For prevention, treatment or amelioration of infection, the thymoquinone antimicrobial agent may be administered or applied at an appropriate frequency. The thymoquinone antimicrobial agent may be administered or applied at least once a day, twice a day, or thrice a day. The thymoquinone antimicrobial agent may be administered or applied at an appropriate frequency for at least 3 days.

For systemic or topical treatment of infection, the amount of thymoquinone administered will depend on multiple factors including age and weight of the subject, severity and size of the wound, the numbers and types of additional active antimicrobial agents contained in the composition administered, and the ratio of active antimicrobial agents in the composition.

The thymoquinone antimicrobial agent may be administered upon detecting emerging antibiotic resistance.

The thymoquinone antimicrobial agent may be used for the treatment of skin infections, such as burn and wound infections, especially those caused by *Acinetobacter baumannii*.

The thymoquinone antimicrobial agent may be used for the treatment of infections in animals. These animal infections may include skin infections, such as burn and wound infections, especially those caused by *Acinetobacter baumannii*.

The following examples illustrate the present teachings:

EXAMPLES

Example 1

Method of Making a Micro-Emulsion Composition with Thymoquinone and Clove Oil

Microemulsion 1

A pharmaceutical composition was prepared including thymoquinone (0.1% w/v), Clove Oil (3% v/v), Tween-20®

(30% v/v) and Water (q.s. up to 100%). Briefly, thymoquinone was dissolved in clove oil to form a first mixture and then tween-20 was added to form a second mixture. The second mixture was vortexed for 1 to 2 minutes and then sonicated for 2-3 minutes in a bath sonicator. After sonication, water was added dropwise to the second mixture, while continuously vortexing to provide a microemulsion. The resulting pharmaceutical composition comprising a microemulsion of thymoquinone, clove oil, Tween-20® and water was further sonicated to remove air bubbles. As is conventionally known, the Tween 20® is a polyoxyethylene sorbitol esteris, a frequently used member of the polysorbate family. These have been used as emulsifying agents for the preparation of stable oil-in-water emulsions.

Example 2

Method of Making a Control Micro-Emulsion Composition with Clove Oil

Microemulsion 2

A pharmaceutical composition was prepared containing clove Oil (3% v/v), Tween-20 (30% v/v), and water (q.s. up to 100%). Briefly, clove oil and Tween-20® were mixed together to form a mixture. The mixture was vortexed for 2 to 3 minutes and then sonicated for 2-3 minutes in a bath sonicator. After sonication, water was added dropwise to the mixture, while continuously vortexing to provide a microemulsion. The resulting pharmaceutical composition comprising a micro-emulsion of clove oil, Tween-20® and water was further sonicated to remove air bubbles.

Example 3

Determination of Antimicrobial Susceptibility (*Acinetobacter baumanii* Strains)

A total of 33 non-duplicate, non-consecutive clinical isolates of Multi-Drug Resistant (MDR) *Acinetobacter baumannii* were collected from burn wards ("AB1-AB33"). *Acinetobacter baumannii* ATCC BAA 747 and *Pseudomonas aeruginosa* ATCC 27853 were used as control strains. The isolates were stored at −80° C. in trypticase soy broth containing 20% glycerol.

Antimicrobial susceptibility tests of the collection of isolates were conducted using the disc diffusion method. The experiment was performed according to the recommendations and guidelines of Clinical Laboratory Standard Institutes (CLSI M100-S24; 2014). Clinical and Laboratory Standards Institute (CLSI), "Performance standards for antimicrobial susceptibility testing; twenty-fourth informational supplement," Document M100-S24, Clinical and Laboratory Standards Institute (CLSI), Wayne, Pa., USA, 2014.

A panel of commercial antibiotic discs (Amoxicillin (AMX), Amoxicillin/clavulanic acid (AMX/CLA), Piperacillin (PIP), Piperacillin/Tazobactam (PIP/TAZ), Ceftazidime (CAZ), Cefotaxime (CTX), Cefepime (FEP), Cefoxitin (FOX), Aztreonam (ATM), Imipenem (IP), Gentamicin (GEN), Amikacin (AK), Neomycin (NEO), Levofloxacin (LEV), Chloramphenicol (CHL), Tetracycline (TET), sulfamethoxazole/trimethoprim (SUL/TRI) was used for susceptibility testing. All commercial antibiotic discs were purchased from BBL (Becton Dickinson, USA).

Forty grams of Mueller-Hinton Agar (MHA) were suspended in 1 Liter distilled water and then boiled to dissolve the powder completely. The medium was sterilized by autoclaving at 121° C. for 15 min. After autoclaving, the medium was cooled to 45° C. and 25 mL of molten agar media was poured into sterile Petri dishes (90 mm diameter) to give a depth of about 4 mm. The surface of the agar was dried to remove excess moisture before use. The plates were stored at 4-8° C. in sealed plastic bags if not used immediately.

The inoculum suspension was prepared by selecting three to five morphologically similar colonies from overnight growth (16-24 h of incubation) on blood agar medium. The colonies were suspended in sterile normal saline to give the density of a McFarland 0.5 standard, which is approximately equivalent to $1-2 \times 10^8$ CFU/mL. The suspension density was measured using a UV spectrophotometer calibrated with a 0.5 McFarland standard. The density of the suspension was adjusted to McFarland 0.5 by addition of saline or more microorganisms. The adjusted inoculum suspension was used within 60 min of preparation.

A sterile cotton swab was dipped into the bacterial suspension and the excess fluid was removed by turning the swab against the inside wall of the tube to avoid over-inoculation of plates. The inoculum was spread evenly over the entire surface of the agar plate by swabbing in three directions.

The predetermined panel of antimicrobial disks was applied firmly on the inoculated Mueller-Hinton agar surface within 15 min of inoculation of the plates by a disc dispenser device. A maximum of six disks were accommodated on a 90-mm circular plate.

Within 15 min of application of antimicrobial disks, the plates were inverted and incubated aerobically at 35-37° C. for 18-20 h.

After incubation, inhibition zones were measured at the point where no obvious growth is detected by the unaided eye when the plate is held about 30 cm from the eye. Inhibition zone diameters were measured to the nearest millimeter with a ruler. The plates were read from the back of the plate with reflected light against a dark background. Zone diameters were interpreted and categorized as susceptible "S", intermediate "I", or resistant "R" according to the CLSI clinical breakpoint tables (see Table 1 and Table 2). "NZ" indicated that no zone of inhibition was observed.

TABLE 1

Antibiotic Susceptibility Testing Against *Acinetobacter Baumannii* Isolates (Inhibition zone in mm)

|     | AMX  | AMX/CLA | PIP  | PIP/TAZ | CAZ  | CTX  | FEP  | FOX  |
| --- | ---- | ------- | ---- | ------- | ---- | ---- | ---- | ---- |
| AB1 | NZ R | NZ R    | 21 S | 22 S    | 20 S | NZ R | 20 S | NZ R |
| AB2 | NZ R | NZ R    | 20 I | 22 S    | 17 I | NZ R | 16 I | NZ R |
| AB3 | NZ R | NZ R    | 32 S | 35 S    | 26 S | 15 I | 18 S | NZ R |
| AB4 | NZ R | NZ R    | 21 S | 22 S    | 21 S | 8 R  | 14 R | NZ R |
| AB5 | NZ R | NZ R    | NZ R | NZ R    | 9 R  | NZ R | 7 R  | NZ R |
| AB6 | NZ R | NZ R    | 18 I | 18 I    | 28 S | 17 I | 21 S | NZ R |

TABLE 1-continued

Antibiotic Susceptibility Testing Against *Acinetobacter Baumannii* Isolates
(Inhibition zone in mm)

|      | AMX  | AMX/CLA | PIP  | PIP/TAZ | CAZ  | CTX  | FEP  | FOX  |
|------|------|---------|------|---------|------|------|------|------|
| AB7  | NZ R | NZ R    | NZ R | NZ R    | NZ R | NZ R | NZ R | NZ R |
| AB8  | NZ R | NZ R    | NZ R | NZ R    | NZ R | NZ R | NZ R | NZ R |
| AB9  | NZ R | NZ R    | 24 S | 25 S    | 21 S | 11 R | 22 S | NZ R |
| AB10 | NZ R | NZ R    | NZ R | NZ R    | NZ R | NZ R | 7 R  | NZ R |
| AB11 | NZ R | NZ R    | NZ R | NZ R    | NZ R | NZ R | NZ R | NZ R |
| AB12 | NZ R | NZ R    | NZ R | NZ R    | NZ R | NZ R | NZ R | NZ R |
| AB13 | NZ R | NZ R    | NZ R | NZ R    | NZ R | NZ R | NZ R | NZ R |
| AB14 | NZ R | NZ R    | NZ R | NZ R    | NZ R | NZ R | NZ R | NZ R |
| AB15 | NZ R | NZ R    | NZ R | NZ R    | NZ R | NZ R | 8 R  | NZ R |
| AB16 | NZ R | NZ R    | 16 R | 25 S    | 32 S | 32 S | 35 S | 22 S |
| AB17 | NZ R | NZ R    | 15 R | 15 R    | 12 R | NZ R | 11 R | NZ R |
| AB18 | NZ R | NZ R    | 8 R  | 8 R     | NZ R | NZ R | NZ R | NZ R |
| AB19 | NZ R | NZ R    | NZ R | NZ R    | NZ R | NZ R | NZ R | NZ R |
| AB20 | NZ R | NZ R    | NZ R | NZ R    | NZ R | NZ R | NZ R | NZ R |
| AB21 | NZ R | NZ R    | NZ R | NZ R    | NZ R | NZ R | NZ R | NZ R |
| AB22 | NZ R | NZ R    | NZ R | NZ R    | NZ R | NZ R | NZ R | NZ R |
| AB23 | NZ R | NZ R    | NZ R | 10 R    | NZ R | NZ R | NZ R | NZ R |
| AB24 | NZ R | NZ R    | NZ R | 9 R     | NZ R | NZ R | 7 R  | NZ R |
| AB25 | NZ R | NZ R    | 10 R | 12 R    | 17 I | 16 I | 10 R | NZ R |
| AB26 | NZ R | NZ R    | NZ R | 9 R     | 15 I | NZ R | 14 R | NZ R |
| AB27 | NZ R | 7 R     | 8 R  | 12 R    | 8 R  | NZ R | 8 R  | NZ R |
| AB28 | 9 R  | 8 R     | 7 R  | 9 R     | 8 R  | NZ R | NZ R | NZ R |
| AB29 | NZ R | NZ R    | NZ R | NZ R    | NZ R | NZ R | NZ R | NZ R |
| AB30 | NZ R | NZ R    | 8 R  | 10 R    | NZ R | NZ R | NZ R | NZ R |
| AB31 | 8 R  | 8 R     | 8 R  | 9 R     | 8 R  | 8 R  | NZ R | 9 R  |
| AB32 | 8 R  | 8 R     | 8 R  | 10 R    | 8 R  | 8 R  | NZ R | NZ R |
| AB33 | NZ R | NZ R    | 22 S | 23 S    | 22 S | 21 I | 18 S | NZ R |
| Break Points |||||||||
| Sensitive    | ≥17   | ≥18   | ≥21   | ≥21   | ≥18   | ≥23   | ≥18   | ≥18   |
| Intermediate | 14-16 | 14-17 | 18-20 | 18-20 | 15-17 | 15-22 | 15-17 | 15-17 |
| Resistant    | ≤13   | ≤13   | ≤17   | ≤17   | ≤14   | ≤14   | ≤14   | ≤14   |

TABLE 2

Antibiotic Susceptibility Testing Against *Acinetobacter Baumannii* Isolates
(Inhibition zone in mm)

|      | ATM  | IP   | GEN  | AK   | NEO  | TET  | CHL  | SUL/TRI | LEV  |
|------|------|------|------|------|------|------|------|---------|------|
| AB1  | NZ R | NZ R | 24 S | 24 S | 23 S | NZ R | NZ R | NZ R    | 30 S |
| AB2  | NZ R | NZ R | 20 S | 20 S | 20 S | 22 S | 24 S | 23 S    | 30 S |
| AB3  | NZ R | NZ R | 24 S | 26 S | 22 S | 22 S | 26 S | 23 S    | 29 S |
| AB4  | NZ R | NZ R | 22 S | 21 S | 27 S | 21 S | 23 S | 20 S    | 30 S |
| AB5  | NZ R | 8 R  | 15 S | 7 R  | 10 R | NZ R | 8 R  | NZ R    | 19 S |
| AB6  | 20 S | 12 R | 26 S | 30 S | 14 I | NZ R | NZ R | NZ R    | 21 S |
| AB7  | NZ R | NZ R | NZ R | NZ R | 12 R | 21 S | NZ R | NZ R    | 14 I |
| AB8  | NZ R | 7 R  | NZ R | 12 R | 11 R | 26 S | 7 R  | NZ R    | 15 I |
| AB9  | NZ R | NZ R | 21 S | 22 S | 20 S | 23 S | 24 S | 25 S    | 28 S |
| AB10 | 13 R | NZ R | NZ R | NZ R | NZ R | NZ R | NZ R | 8 R     | 14 I |
| AB11 | NZ R | NZ R | NZ R | NZ R | NZ R | NZ R | NZ R | NZ R    | 11 R |
| AB12 | NZ R | 11 R | 12 R | 21 S | 15 S | NZ R | NZ R | NZ R    | 10 R |
| AB13 | NZ R | 9 R  | NZ R | 22 S | 9 R  | NZ R | NZ R | NZ R    | 8 R  |
| AB14 | NZ R | 15 R | NZ R | NZ R | NZ R | 24 S | NZ R | NZ R    | 11 R |
| AB15 | 11 R | NZ R | 20 S | 13 R | 13 I | 19 S | 10 R | NZ R    | 15 I |
| AB16 | 33 S | 34 S | 18 S | 19 S | NZ R | NZ R | 30 S | 26 S    | NZ R |
| AB17 | 15 R | 15 R | 24 S | 22 S | 20 S | 21 S | 13 I | NZ R    | 11 R |
| AB18 | 10 R | NZ R | 17 S | 14 R | 15 S | 20 S | 8 R  | NZ R    | 13 R |
| AB19 | 8 R  | NZ R | 20 S | 14 R | 13 I | 17 S | 8 R  | NZ R    | 11 R |
| AB20 | NZ R | 15 R | NZ R | NZ R | NZ R | 28 S | NZ R | NZ R    | 13 R |
| AB21 | 7 R  | NZ R | 17 S | 11 R | 13 I | 19 S | NZ R | NZ R    | 14 I |
| AB22 | NZ R | 15 R | NZ R | NZ R | 7 R  | 20 S | NZ R | NZ R    | 14 I |
| AB23 | NZ R | 20 I | NZ R | NZ R | 10 R | 23 S | NZ R | NZ R    | 11 R |
| AB24 | NZ R | NZ R | 19 S | 14 R | 14 I | 19 S | 8 R  | NZ R    | 12 R |
| AB25 | 13 R | 23 S | 19 S | NZ R | 8 R  | 25 S | NZ R | 21 S    | 14 I |
| AB26 | 12 R | 22 S | NZ R | 18 S | 20 S | NZ R | 25 S | NZ R    | NZ R |
| AB27 | NZ R | 9 R  | 8 R  | 9 R  | 9 R  | NZ R | 8 R  | NZ R    | 8 R  |
| AB28 | NZ R | 8 R  | 20 S | 15 I | 15 S | 20 S | 14 I | NZ R    | 15 I |
| AB29 | NZ R | 9 R  | 20 S | 15 I | 15 S | 19 S | 12 R | NZ R    | 15 I |
| AB30 | 9 R  | 9 R  | 20 S | 15 I | 15 S | 20 S | 11 R | NZ R    | 15 I |
| AB31 | NZ R | 9 R  | 8 R  | NZ R | 8 R  | NZ R | 8 R  | NZ R    | 10 R |

TABLE 2-continued

Antibiotic Susceptibility Testing Against *Acinetobacter Baumannii* Isolates
(Inhibition zone in mm)

|  | ATM | IP | GEN | AK | NEO | TET | CHL | SUL/TRI | LEV |
|---|---|---|---|---|---|---|---|---|---|
| AB32 | 8 R | 18 R | NZ R | NZ R | 10 R | 28 S | 9 R | NZ R | 18 S |
| AB33 | 9 R | NZ R | 20 S | 25 S | 20 S | 24 S | 18 S | 24 S | 30 S |
| Break Point | | | | | | | | | |
| Sensitive | ≥22 | ≥22 | ≥15 | ≥17 | ≥15 | ≥15 | ≥18 | ≥16 | ≥17 |
| Intermediate | 16-21 | 19-21 | 13-14 | 15-16 | 13-14 | 12-14 | 13-17 | 11-15 | 14-16 |
| Resistant | ≤15 | ≤18 | ≤12 | ≤14 | ≤12 | ≤11 | ≤12 | ≤10 | ≤13 |

Example 4

Thymoquinone MIC Determination

Minimum Inhibitory Concentration (MIC) is the lowest concentration of an antimicrobial agent that prevents visible growth of a microorganism in an agar or broth dilution susceptibility test. MIC of thymoquinone was determined by the broth dilution method against 33 MDR *Acinetobacter baumannii* strains and standard sensitive culture collection strain of *Acinetobacter baumannii* and *Pseudomonas aeruginosa*. The MIC of gentamicin was deter lined by broth dilution method against six MDR *Acinetobacter baumannii* strains and standard sensitive culture collection strains of *Acinetobacter baumannii* and *Pseudomonas aeruginosa*. MIC testing was performed according to the recommendations and guidelines of Clinical Laboratory Standard Institutes (CLSI M07-A9; 2012). Clinical and Laboratory Standards Institute (CLSI), "Methods for Dilution Antimicrobial Susceptibility Tests for Bacteria That Grow Aerobically; Approved Standard," Document M07-A9, Clinical and Laboratory Standards Institute (CLSI), Wayne, Pa., USA, 2012.

Twenty-one grams of Mueller-Hinton Broth (MHB) was suspended in 1 Liter distilled water and then boiled to dissolve the powder completely. The medium was sterilized by autoclaving at 121° C. for 15 min. After autoclaving, the medium was cooled to room temperature before use or stored in the fridge until used.

Thymoquinone was weighed and dissolved in Dimethyl sulfoxide (DMSO) to produce a thymoquinone stock solution with a concentration of 5,120 µg/ml. Gentamicin sulfate was weighed and dissolved in water to produce a gentamicin sulfate stock solution with a concentration of 5,120 µg/ml, equivalent to gentamicin base.

Dilutions of thymoquinone and gentamicin sulfate stock solutions were prepared volumetrically in the MHB as follows:

One mL of original stock solution (5,120 µg/ml) was added to 9 ml sterile MHB to give the working first dilution (512 µg/mL). 12 sterile 7 mL PJ tubes were arranged in a rack in a row. Each tube contained one mL sterile MHB. Ten tubes were labeled as 128 µg/mL, 64 µg/mL, 32 µg/mL, 16 µg/mL, 8 µg/mL, 4 µg/mL, 2 µg/mL, 1 µg/mL, 0.5 µg/mL and 0.25 µg/mL. The eleventh and twelfth tubes were labeled as positive and negative control, respectively.

The working dilution (512 µg/mL) was serially diluted to give two-fold dilutions. One mL of the working dilution (512 µg/mL) was dispensed in the first tube (labeled as 128 µg/mL) to give a concentration of 256 µg drug/mL MHB. One mL of the first tube was added to the second tube (labeled as 64 µg/mL) to give a concentration of 128 µg drug/mL MHB. One mL of the second tube was transferred to the third tube (labeled as 32 µg/mL) to give a concentration of 64 µg drug/mL MHB. One mL of the third tube was added to the fourth tube (labeled as 16 µg/mL) to give a concentration of 32 µg drug/mL MHB. One mL of the fourth tube was dispensed in the fifth tube (labeled as 8 µg/mL) to give a concentration of 16 µg drug/mL MHB. One mL of the fifth tube was dispensed in the sixth tube (labeled as 4 µg/mL) to give a concentration of 8 µg drug/mL MHB. One mL of the sixth tube was added to the seventh tube (labeled as 2 µg/mL) to give a concentration of 4 µg drug/mL MHB. One mL of the seventh tube was added to the eighth tube (labeled as 1 µg/mL) to give a concentration of 2 µg drug/mL MHB. One mL of the eighth tube was transferred to the ninth tube (labeled as 0.5 µg/mL) to give a concentration of 1 µg drug/mL MHB. One mL of the ninth tube was transferred to the tenth tube (labeled as 0.25 µg/mL) to give a concentration of 0.5 µg drug/mL MHB. The contents were mixed thoroughly by pipetting up and down three times. One mL of the content of the tenth tube was discarded.

The inoculum suspensions (at $1-2 \times 10^8$ CFU/mL) were diluted 1:100 in MHB to obtain $1 \times 10^6$ CFU/mL. One mL of the diluted inoculum suspension ($1 \times 10^6$ CFU/mL) was transferred to each tube except tube 12. This resulted in 1:2 dilutions of each drug concentration and a 1:2 dilution of the inoculums (to $5 \times 10^5$ CFU/mL).

All inoculated tubes were incubated for 16-20 hours at 37° C. aerobically. After this incubation period, MIC was determined manually by observing the lowest concentration of antimicrobial agent showing no visible growth (turbidity). The MIC of thymoquinone against *Acinetobacter baumannii* isolates and standard strain of *Acinetobacter baumannii* ATCC BAA 747 is presented in Table 3. The MIC of gentamicin against *Acinetobacter baumannii* isolates and standard strain of *Acinetobacter baumannii* ATCC BAA 747 is presented in Table 4. The MIC of thymoquinone and gentamicin against *Pseudomonas aeruginosa* ATCC 27853 was found to be 64 µg/ml and ≤2 µg/ml, respectively.

TABLE 3

MIC of Thymoquinone Against *Acinetobacter baumannii* Isolates (µg/ml)

| Isolate | MIC |
|---|---|
| AB1 | 32 |
| AB2 | 32 |

TABLE 3-continued

MIC of Thymoquinone Against *Acinetobacter baumannii* Isolates (μg/ml)

| Isolate | MIC |
| --- | --- |
| AB3 | 32 |
| AB4 | 32 |
| AB5 | 32 |
| AB6 | 64 |
| AB7 | 32 |
| AB8 | 32 |
| AB9 | 32 |
| AB10 | 16 |
| AB11 | 32 |
| AB12 | 32 |
| AB13 | 32 |
| AB14 | 32 |
| AB15 | 32 |
| AB16 | 64 |
| AB17 | 64 |
| AB18 | 32 |
| AB19 | 64 |
| AB20 | 64 |
| AB21 | 32 |
| AB22 | 64 |
| AB23 | 32 |
| AB24 | 32 |
| AB25 | 32 |
| AB26 | 64 |
| AB27 | 64 |
| AB28 | 64 |
| AB29 | 64 |
| AB30 | 32 |
| AB31 | 32 |
| AB32 | 32 |
| AB33 | 32 |
| *A.b.* ATCC BAA 747 | 32 |
| *P a.* ATCC 27853 | 64 |

TABLE 4

MIC of Gentamicin Sulfate Against *Acinetobacter baumannii* Isolates (μg/ml)

| Isolates | MIC |
| --- | --- |
| AB7 | 32 |
| AB8 | 64 |
| AB10 | 32 |
| AB11 | 32 |
| AB12 | 32 |
| AB13 | 32 |
| *A. baumannii* ATCC BAA 747 | 1 |
| *P. aeruginosa* ATCC 27853 | ≤2 |

Example 5

Determination of MIC of the Micro-Emulsion of Example 1

Nine sterile 7 mL PJ tubes were arranged in a rack in a row. Each tube contained one mL sterile MHB. Seven tubes were labeled as 7.847 mg+256 μg/mL, 3.923 mg+128 μg/mL, 1.961 mg+64 μg/mL, 0.980 mg+32 μg/mL, 0.490 mg+16 μg/mL, 0.245 mg+8 μg/mL and 0.122 mg+4 μg/mL. The eighth and ninth tubes were labeled as positive and negative controls, respectively.

The micro-emulsion made according to Example 1 was serially diluted to give two-fold dilutions as follows: one mL of the micro-emulsion of Example 1 was dispensed in the first tube (labeled as 7.847 mg+256 μg/mL) to give a concentration of 15.69 mg+512 μg drug/mL MHB. One mL of the first tube was added to the second tube (labeled as 3.923 mg+128 μg/mL) to give a concentration of 7.847 mg+256 μg drug/mL MHB. One mL of the second tube was transferred to the third tube (labeled as 1.961 mg+64 μg/mL) to give a concentration of 3.923 mg+128 drug/mL MHB. One mL of the third tube was added to the fourth tube (labeled as 0.980 mg+32 μg/mL) to give a concentration of 1.961 mg+64 drug/mL MHB. One mL of the fourth tube was dispensed in the fifth tube (labeled as 0.490 mg+16 μg/mL) to give a concentration of 0.980 mg+32 drug/mL MHB. One mL of the fifth tube was dispensed in the sixth tube (labeled as 0.245 mg+8 μg/mL) to give a concentration of 0.490 mg+16 μg drug/mL MHB. One mL of the sixth tube was added to the seventh tube (labeled as 0.122 mg+4 μg/mL) to give a concentration of 0.245 mg+8 μg drug/mL MHB. One mL of the content of the seventh tube was discarded. Inoculum suspensions (at 1-2×10⁸ CFU/mL) were diluted 1:100 in MHB to obtain 1×10⁶ CFU/mL. One mL of the diluted inoculum suspension (1×10⁶ CFU/mL) was transferred to each tube except tube number nine. This resulted in a 1:2 dilutions of each drug concentration and a 1:2 dilution of the inoculums (5×10⁵ CFU/mL).

Another nine sterile 7 mL PJ tubes were arranged in a rack in a row. Each tube contained one mL sterile MHB. Seven tubes were labeled as 7.847 mg/mL, 3.923 mg/mL, 1.961 mg/mL, 0.980 mg/mL, 0.490 mg/mL, 0.245 mg/mL and 0.122 mg/mL. The eighth and ninth tubes were labeled as positive and negative control, respectively.

The micro-emulsion of Example 2 was serially diluted to give two-fold dilutions as follows: one mL of the micro-emulsion of Example 2 was dispensed in the first tube (labeled as 7.847 mg/mL) to give a concentration of 15.69 mg drug/mL MHB. One mL of the first tube was added to the second tube (labeled as 3.923 mg/mL) to give a concentration of 7.847 mg drug/mL MHB. One mL of the second tube was transferred to the third tube (labeled as 1.961 mg/mL) to give a concentration of 3.923 mg drug/mL MHB. One mL of the third tube was added to the fourth tube (labeled as 0.980 mg/mL) to give a concentration of 1.961 mg drug/mL MHB. One mL of the fourth tube was dispensed in the fifth tube (labeled as 0.490 mg/mL) to give a concentration of 0.980 mg drug/mL MHB. One mL of the fifth tube was dispensed in the sixth tube (labeled as 0.245 mg/mL) to give a concentration of 0.490 mg drug/mL MHB. One mL of the sixth tube was added to the seventh tube (labeled as 0.122 mg/mL) to give a concentration of 0.245 mg drug/mL MHB. One mL of the content of seventh tube was discarded. Inoculum suspensions (at $1$-$2\times10^8$ CFU/mL) were diluted 1:100 in MHB to obtain $1\times10^6$ CFU/mL. One mL of the diluted inoculum suspension ($1\times10^6$ CFU/mL) was transferred to each tube except tube number nine. This resulted in a 1:2 dilution of each drug concentration and a 1:2 dilution of the inoculums (to $5\times10^5$ CFU/mL).

All inoculated tubes were incubated for 16-20 hours at 37° C. aerobically. After this incubation period, MIC was determined manually by observing the lowest concentration of antimicrobial agent showing no visible growth (turbidity). The MIC of the micro-emulsion of Example 1 and the micro-emulsion of Example 2 against *Acinetobacter baumannii* isolates is presented in Table 5.

TABLE 5

MIC of Example 1, Example 2, and Thymoquinone Against Multidrug Resistant *Acinetobacter baumannii* Isolates (μg/ml)

|  | Isolate 121 | Isolate 127 | Isolate 129 |
| --- | --- | --- | --- |
| Example 1 | 16 ± 490.4 | 16 ± 490.4 | 16 ± 490.4 |
| Example 2 | 1961.8 | 980.9 | 980.9 |
| Thymoquinone | 64 | 32 | 32 |

It is to be understood that a method for preventing, treating, or ameliorating microbial infections is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A pharmaceutical composition, comprising from about 0.01% to about 1.0% w/v thymoquinone, from about 2% to about 6% by volume oil, from about 25% to about 40% by volume surfactant, and water, wherein the pharmaceutical composition is formulated as a microemulsion.

2. The pharmaceutical composition according to claim 1, wherein the surfactant comprises a polyoxyethylene sorbitol ester and the oil comprises Clove Oil.

3. The pharmaceutical composition according to claim 2, wherein the pharmaceutical composition comprises 0.1% w/v thymoquinone, 3% by volume clove oil, 30% by volume of a polyoxyethylene sorbitol ester, and the remainder of the pharmaceutical composition comprises water.

4. The pharmaceutical composition according to claim 1, further comprising at least one supplemental antimicrobial agent selected from the group consisting of an aminoglycoside, an ansamycin, a carbapenem, a cephalosporin, a glycopeptide, a lincosamide, a lipopeptide, a macrolide, a monobactam, a nitrofuran, an oxazolidinone, a penicillin, a penicillin combination, a polypeptide, a quinolone, a fluoroquinolone, a sulfonamide, a tetracycline, an anti-mycobacterial, an antibiotic, an essential oil, an active constituent of an essential oil, myrrh, and an active ingredient of myrrh.

* * * * *